US011301720B2

United States Patent
Levanony et al.

(10) Patent No.: US 11,301,720 B2
(45) Date of Patent: Apr. 12, 2022

(54) TRAINING SET ENRICHMENT WITH INSIGNIFICANTLY-ABNORMAL MEDICAL IMAGES

(71) Applicant: International Business Machines Corporation, Armonk, NY (US)

(72) Inventors: Dana Levanony, Tel-Aviv (IL); Shaked Perek, Givatayim (IL); Efrat Hexter, Beit Shemesh (IL)

(73) Assignee: International Business Machines Corporation, Armonk, NY (US)

( * ) Notice: Subject to any disclaimer, the term of this patent is extended or adjusted under 35 U.S.C. 154(b) by 23 days.

(21) Appl. No.: 16/860,086

(22) Filed: Apr. 28, 2020

(65) Prior Publication Data

US 2021/0334591 A1 Oct. 28, 2021

(51) Int. Cl.
*G06T 7/00* (2017.01)
*G06T 5/00* (2006.01)
(Continued)

(52) U.S. Cl.
CPC .......... *G06K 9/6256* (2013.01); *G06K 9/628* (2013.01); *G06N 3/08* (2013.01); *G06T 5/005* (2013.01);
(Continued)

(58) Field of Classification Search
CPC . G06T 7/11; G06T 7/12; G06T 7/0012; G06T 7/0014; G06T 7/0016; G06T 5/005;
(Continued)

(56) References Cited

U.S. PATENT DOCUMENTS 8,682,810 B2 * 3/2014 Zhang ................ G06K 9/00147
706/12
11,024,031 B1 * 6/2021 Nozaki ................ G06T 7/0016
(Continued)

FOREIGN PATENT DOCUMENTS

WO 2019215109 A1 11/2019
WO WO-2019215109 A1 * 11/2019 ......... G06K 9/00201
(Continued)

OTHER PUBLICATIONS

Juergen Carstensa et al., "Multiple Instance Learning Based Self Learning Approach to Reduce Human Effort in Marking Regions of Interest in Imaging Applications," An IP.com Prior Art Database Technical Disclosure No. IPCOM000213368D, Dec. 13, 2011.
(Continued)

*Primary Examiner* — Sean M Conner
*Assistant Examiner* — Stephen M Brinich
(74) *Attorney, Agent, or Firm* — Dvir Gassner (57) ABSTRACT

A method including: automatically detecting, using at least one machine learning algorithm, one or more abnormalities depicted in a medical image of a patient; automatically determining whether the one or more abnormalities have remained temporally and unchanged, based on an older medical image of the patient; and upon determining that the one or more abnormalities have remained temporally and spatially unchanged: automatically inpainting the one or more abnormalities in the medical image, and automatically enrich a new training set with the inpainted medical image.

20 Claims, 2 Drawing Sheets

(51) Int. Cl.
*G06T 7/11* (2017.01)
*G16H 50/20* (2018.01)
*G16H 30/40* (2018.01)
*G06K 9/62* (2022.01)
*G06N 3/08* (2006.01)

(52) U.S. Cl.
CPC .............. *G06T 7/0016* (2013.01); *G06T 7/11* (2017.01); *G16H 30/40* (2018.01); *G16H 50/20* (2018.01); *G06T 2207/20081* (2013.01); *G06T 2207/20084* (2013.01)

(58) Field of Classification Search
CPC G06T 2207/20081; G06T 2207/20084; G16H 30/40; G16H 50/20; G16H 50/30; G16H 50/50; G06K 9/6256; G06K 9/628
USPC .................................. 382/128, 131–132, 100
See application file for complete search history.

(56) References Cited

U.S. PATENT DOCUMENTS

| | | | |
|---|---|---|---|
| 2018/0025489 A1* | 1/2018 | Tiwari | G06T 7/0012 600/420 |
| 2018/0050222 A1* | 2/2018 | Feain | A61B 6/5288 |
| 2018/0365824 A1* | 12/2018 | Yuh | G06T 7/0012 |
| 2019/0090834 A1* | 3/2019 | Pauly | G06T 3/0031 |
| 2019/0163955 A1* | 5/2019 | Asif | G06T 7/0012 |
| 2020/0163641 A1* | 5/2020 | Amit | G16H 30/20 |
| 2020/0202529 A1* | 6/2020 | Hart | G06N 3/08 |

FOREIGN PATENT DOCUMENTS

| | | | |
|---|---|---|---|
| WO | 2019238804 A1 | 12/2019 | |
| WO | WO-2019238804 A1 * | 12/2019 | .............. G06K 9/34 |

OTHER PUBLICATIONS

Neeraj Sharma et al., "Automated Medical Image Segmentation Techniques," Journal of Medical Physics, vol. 35, No. 1, Apr. 3-14, 2010.

R. J. Ramteke et al., "Automatic Medical Image Classification and Abnormality Detection Using K-Nearest Neighbour," International Journal of Advanced Computer Research, vol. 2 No. 4 Issue 6, Dec. 2012.

* cited by examiner

TRAINING SET ENRICHMENT WITH INSIGNIFICANTLY-ABNORMAL MEDICAL IMAGES

BACKGROUND

The invention relates to the field of artificial intelligence (AI) in medical imaging.

With the advent of AI technology, analysis of medical images, such as X-Ray, CT (Computerized Tomography), MRI (Magnetic Resonance Imaging), and ultrasound images is becoming increasingly automated. Machine learning algorithms are now able to reliably perform tasks such as area segmentation, parameter measurement, pathology detection, and even diagnosis of various medical conditions. The use of these algorithms in medical imagery analysis increases productivity, helps standardize processes at the medical facility, and often improves diagnosis accuracy.

Machine learning algorithms in the medical field typically rely on large, high-quality datasets of medical images for their training, but such datasets are a rather scarce commodity. Obtaining a good dataset usually involves a labor-intensive, costly, and sometimes government-regulated process of acquiring access to a collection of existing medical images, carefully designing criteria for automated selection of suitable images out of the vast collection, and labeling the selected images manually, by medical experts.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

One embodiment is directed to a method comprising operating at least one hardware processor to: automatically detect, using at least one machine learning algorithm, one or more abnormalities depicted in a medical image of a patient; automatically determine whether the one or more abnormalities have remained temporally unchanged, based on an older medical image of the patient; and upon determining that the one or more abnormalities have remained temporally unchanged: automatically inpaint the one or more abnormalities in the medical image, to enable enrichment of a new training set with the inpainted medical image.

Another embodiment relates to a system comprising: (a) at least one hardware processor; and (b) a non-transitory computer-readable storage medium having program code embodied therewith, the program code executable by said at least one hardware processor to: automatically detect, using at least one machine learning algorithm, one or more abnormalities depicted in a medical image of a patient; automatically determine whether the one or more abnormalities have remained temporally unchanged, based on an older medical image of the patient; and upon determining that the one or more abnormalities have remained temporally unchanged: automatically inpaint the one or more abnormalities in the medical image, to enable enrichment of a new training set with the inpainted medical image.

A further embodiment is directed to a computer program product comprising a non-transitory computer-readable storage medium having program code embodied therewith, the program code executable by at least one hardware processor to: automatically detect, using at least one machine learning algorithm, one or more abnormalities depicted in a medical image of a patient; automatically determine whether the one or more abnormalities have remained temporally unchanged, based on an older medical image of the patient; and upon determining that the one or more abnormalities have remained temporally unchanged: automatically inpaint the one or more abnormalities in the medical image, to enable enrichment of a new training set with the inpainted medical image.

In some embodiments, the detection of the one or more abnormalities by the at least one machine learning algorithm comprises: applying a machine learning classifier to the medical image of a patient, wherein the machine learning classifier is configured to classify medical images as normal or abnormal, and wherein the application of the machine learning classifier to the medical image results in classification of the medical image as abnormal; and segmenting the one or more abnormalities in the medical image, using an artificial neural network (ANN) configured for segmentation.

In some embodiments, the method further comprises, or the program code is further executable for: prior to applying the machine learning classifier: training the machine learning classifier to detect abnormalities, based on a training set which comprises medical images that are each manually labeled as normal or abnormal; and prior to segmenting the one or more abnormalities: training the ANN to segment abnormalities, based on a training set which comprises medical images in which abnormalities are manually segmented.

In some embodiments, the determination of whether the one or more abnormalities have remained temporally unchanged comprises comparing the segmented one or more abnormalities with a corresponding area in the older medical image.

In some embodiments, the detection of the one or more abnormalities by the at least one machine learning algorithm comprises: segmenting the one or more abnormalities in the medical image, using an artificial neural network (ANN) configured for segmentation of abnormalities.

In some embodiments, the method further comprises, or the program code is further executable for: prior to segmenting the one or more abnormalities: training the ANN to segment abnormalities, based on a training set which comprises medical images in which abnormalities are manually segmented.

In some embodiments, the determination of whether the one or more abnormalities have remained temporally unchanged comprises comparing the segmented one or more abnormalities with a corresponding area in the older medical image.

In some embodiments, the determination of whether the one or more abnormalities have remained temporally unchanged is based on detecting at least one of: a size change, a color change, and a texture change.

In some embodiments, the at least one machine learning algorithm is configured to detect abnormalities that are selected from the group consisting of: benign lesions, artificial implants, injuries, and interventional tissue modifications.

In some embodiments, the method further comprises, or the program code is further executable for: repeating the detection, determination, and inpainting steps for multiple medical images of multiple patients, wherein the inpainted medical images are used to enrich a single new training set;

manually labeling each of the inpainted medical images as normal; adding, to the single new training set, additional medical images that are labeled as abnormal; and training a new machine learning classifier based on the single new training set.

In some embodiments, the new machine learning classifier is configured, following its training, to detect abnormalities that are selected from the group consisting of: malignant lesions, and premalignant lesions.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein is a technique, embodied in a method, system, and computer program product, for enrichment of a machine learning training set with medical images that are seemingly unsuitable to be trained upon, but can be successfully identified and then sanitized to make them appropriate for inclusion in the training set.

Advantageously, the technique allows for enlarging the pool of training-grade medical images with images that may have been otherwise categorically excluded from the training set. According to the technique, medical images that have a certain abnormal 'finding' in them are first identified, and then analyzed to determine whether that finding is just of an insignificantly-abnormal feature. The analysis may include comparing a detected abnormal finding against an older medical image of the same patient; if that exact finding also exists in the older image, namely—it has remained temporally unchanged, this indicates that the newer image can be safely trained upon for a new machine learning task (of course, after removing that finding so that it does not bias the resulting classifier).

In a typical use case of the present technique, a computerized collection of medical images may be accessed, for example a hospital Picture Archiving and Communication System (PACS) which stores images in conjunction with metadata such as radiological and pathological reports. Let us assume, for example, that the intended task is to train a machine learning classifier so that it can analyze mammograms and ultimately classify them as "normal" or "precancerous/cancerous." This requires compiling a training set of ground-truth normal and precancerous/cancerous images that are correspondingly labeled. Obtaining the precancerous/cancerous images is rather straightforward—the collection may be suitably queried, to return images whose pathology report (e.g., of a needle biopsy conducted following suspicions raised in the radiological report) indicate precancer or cancer. To obtain the normal images, conventionally, the collection is typically queried for images with no abnormal findings whatsoever in their metadata—to ensure that the normal ground-truth examples will be as clean and untainted as possible. However, the number of available mammograms which satisfy this strict criterion for normalcy may be too low to form a robust training set; radiological reports of many mammograms still indicate certain abnormalities such as scars, architectural distortions, etc., which might bias any classifier trained based on them. The present technique, advantageously, allows obtaining also those images with non-cancerous and non-precancerous abnormalities, identifies images with insignificantly-abnormal findings in them (by the aforementioned comparison with older images), and sanitizes these images by removing these findings, so that the images can properly serve as ground-truth normal images.

The term "medical image" (referred to below as "image" for reasons of brevity), as used herein, relates to a digital image acquired using any known medical imaging modality, such as X-Ray, CT, MRI, PET (Positron Emission Tomography), SPECT (Single Photon Emission Computed Tomography), PEM (Positron Emission Mammography), OCT (Optical Coherence Tomography), ultrasound, etc. The image may be two- or three-dimensional, and may depict any human or animal anatomy.

Figure 1:
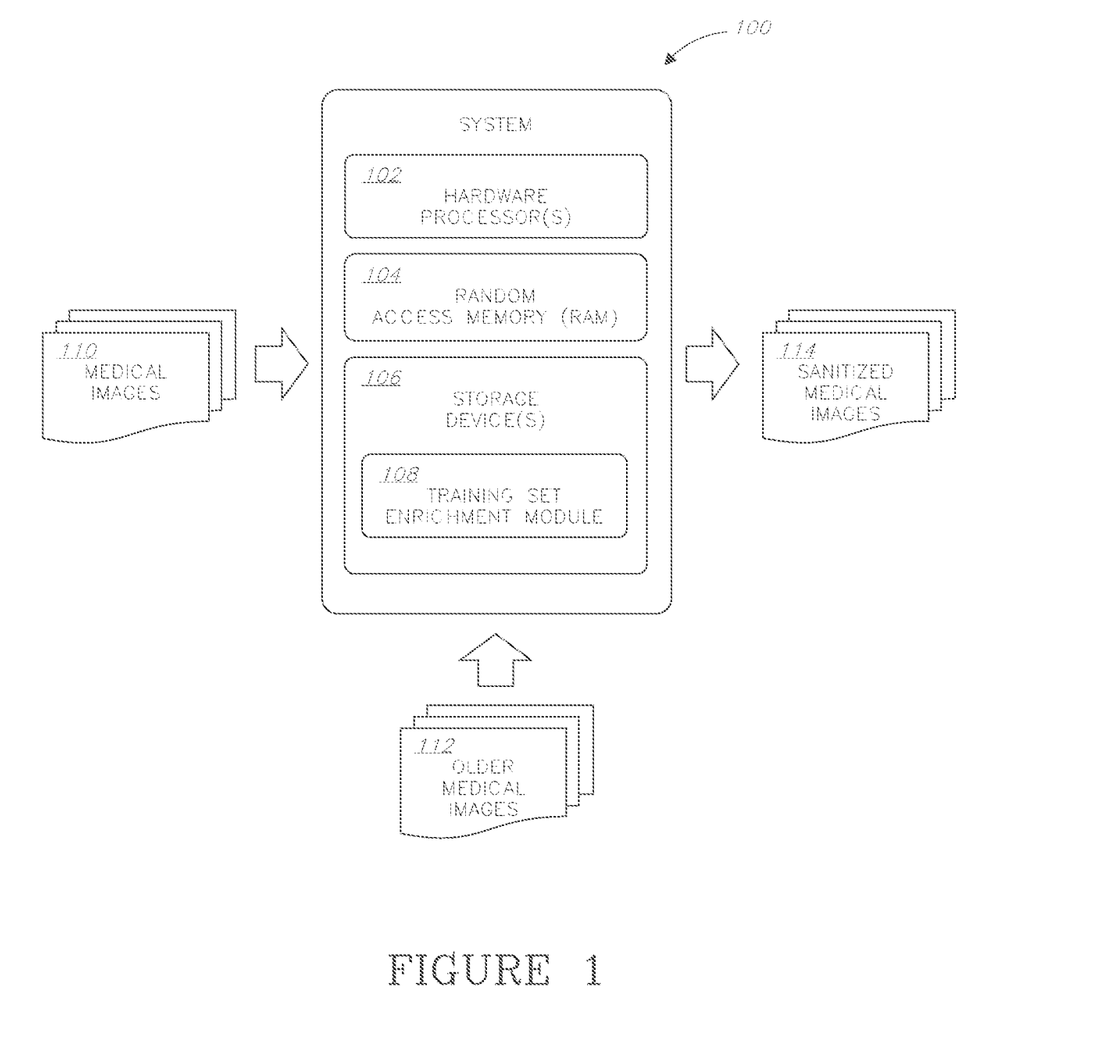
FIG. 1 is a block diagram of an exemplary system for enrichment of a machine learning training set, according to an embodiment.

Reference is now made to FIG. 1, which shows a block diagram of an exemplary system 100 for enrichment of a machine learning training set, according to an embodiment. System 100 may include one or more hardware processor(s) 102, a random-access memory (RAM) 104, and one or more non-transitory computer-readable storage device(s) 106.

Storage device(s) 106 may have stored thereon program instructions and/or components configured to operate hardware processor(s) 102. The program instructions may include one or more software modules, such as a training set enrichment module 108. The software components may include an operating system having various software components and/or drivers for controlling and managing general system tasks (e.g., memory management, storage device control, power management, etc.), and facilitating communication between various hardware and software components.

System 100 may operate by loading instructions of training set enrichment module 108 into RAM 104 as they are being executed by processor(s) 102. The instructions of training set enrichment module 108 may cause system 100 to receive images 110, analyze them, obtain older images 112 whenever necessary for the analysis, and output corrected images 114 that are added as ground-truth normal images to a training set for a machine learning classifier.

Optionally, system 100 also includes a module (not shown) which contains program instructions to train that machine learning classifier based on the corrected images 114 and on additional images comprised in the training set.

System 100 as described herein is only an exemplary embodiment of the present invention, and in practice may be implemented in hardware only, software only, or a combination of both hardware and software. System 100 may have more or fewer components and modules than shown, may combine two or more of the components, or may have a different configuration or arrangement of the components. System 100 may include any additional component enabling it to function as an operable computer system, such as a motherboard, data busses, power supply, a network interface card, a display, an input device (e.g., a keyboard, pointing device, touch-sensitive display), etc. (not shown). Moreover, components of system 100 may be co-located or distributed, or the system could run as one or more cloud computing "instances," "containers," and/or "virtual machines," as known in the art.

Figure 2:
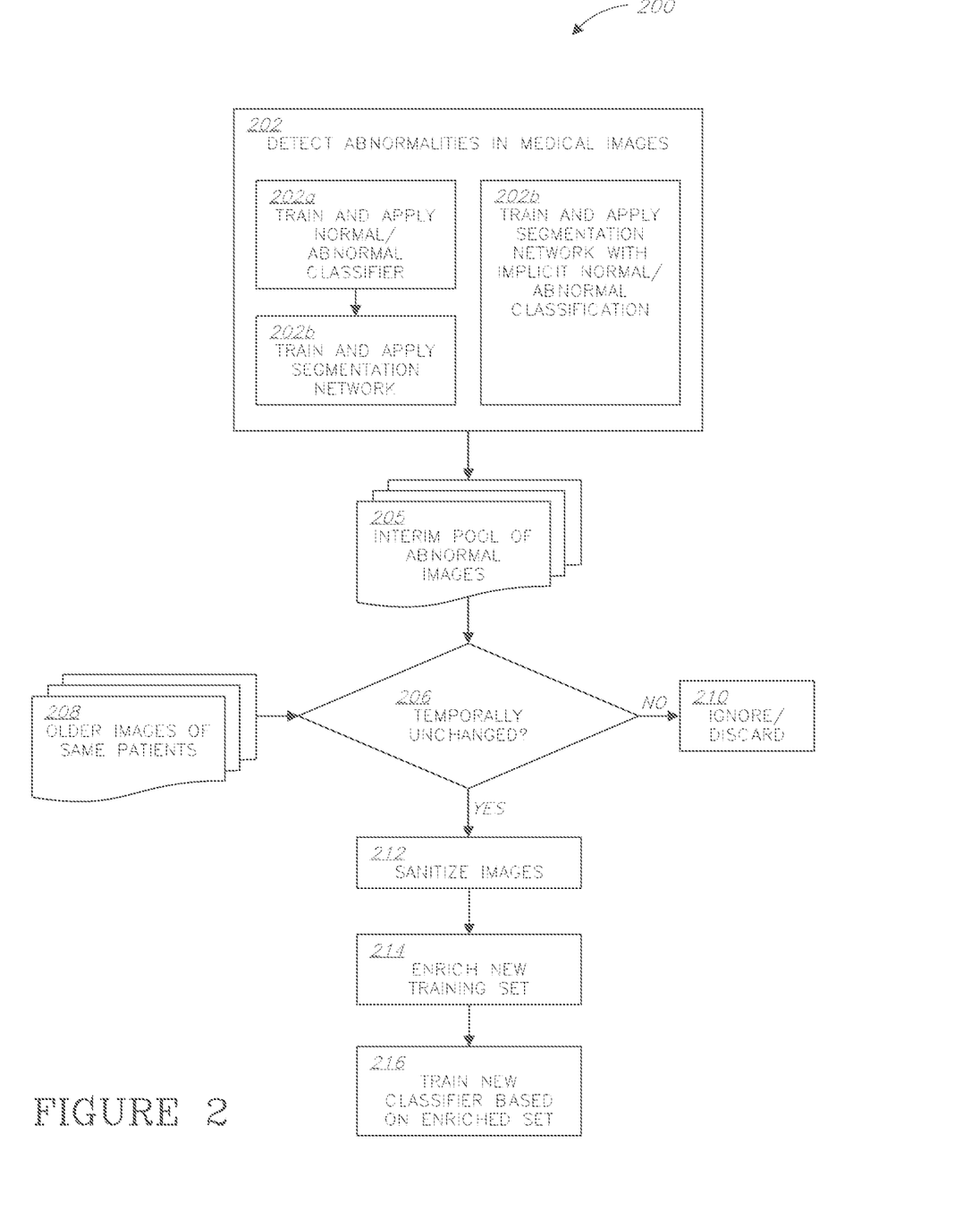
FIG. 2 is a flowchart of a method for enriching a machine learning training set, according to an embodiment.

The instructions of training set enrichment module 108 are now discussed with reference to the flowchart of FIG. 2, which illustrates a method 200 for training set enrichment, in accordance with an embodiment.

Steps of method 200 may either be performed in the order they are presented or in a different order (or even in parallel), as long as the order allows for a necessary input to a certain step to be obtained from an output of an earlier step. In addition, the steps of method 200 are performed automatically (e.g., by system 100 of FIG. 1), unless specifically stated otherwise.

In a step 202, at least one machine learning algorithm is used for detecting one or more abnormalities depicted in an image of a patient. This detection may be performed, for example, according to one of the following options: One option, discussed below with reference to sub-steps 202a-b, is to train and then apply a classifier to detect the one or more abnormalities, and then to train and then apply a segmentation artificial neural network (ANN) to segment the detected one or more abnormalities. Another option, discussed with reference to sub-step 202c, is to only train and then apply a segmentation ANN, to segment one or more areas which are implicitly associated with abnormalities.

In sub-step 202a, accordingly, a machine learning classifier (hereinafter "classifier") may be trained to detect one or more abnormalities depicted in an image. This classifier should not be confused with a later classifier which is ultimately trained based on an enriched training set created by method 200. Rather, the classifier of sub-step 202a participates just in an early step of identifying images which could potentially be sanitized and used to enrich the later training set.

The classifier trained in sub-step 202a may be of any suitable type, for example an artificial neural network (ANN) such as a deep neural network (DNN) or more specifically a convolutional neural network (CNN), as known in the art.

To train this classifier, a training set of images may be obtained, which includes both images with no depicted abnormalities at all, and images with depicted abnormalities that are localized in nature, namely—image features that each extend over a contiguous area in the respective image. For example, such feature may be the result of interventional tissue modification (e.g., scar, unnatural anatomical structure, etc.), of natural biological processes (e.g., lesion, calcification, degeneration, inflammation etc.), of injury (e.g., fracture, hemorrhage, etc.), or depict an artificial implant (e.g., tack, suture, mesh, screw, plate, anchor, pacemaker, dental filling, etc.), to name some examples.

Images of both these types are optionally manually reviewed prior to their inclusion in the training set, to ensure they satisfy the above criteria for depicted abnormalities and no depicted abnormalities. In addition, the images may undergo manual labeling, to label each one of them as "normal" (i.e., no abnormalities depicted) or "abnormal" (i.e. one or more abnormalities depicted), or with any other labels denoting the same.

The classifier may then be trained based on this labeled training set, using conventional techniques. The result is a classifier able to classify every input image as "normal" or "abnormal," or as differently-named classes which denote the same.

Further is sub-step 202a, the trained classifier is applied to an image of a patient, to classify the image as depicting one or more abnormalities, or as not depicting any abnormalities. The classification may be repeated for multiple images of multiple patients.

Images classified as "normal" are optionally added to a training set whose enrichment is desired (the "enriched training set"), since these images likely require no further analysis to conclude that they are completely devoid of any abnormalities. To better ensure that this is the case, manual review of these images may be conducted, if so desired.

In sub-step 202b, a segmentation ANN (hereinafter "segmentation network") may be trained to segment one or more abnormalities depicted in an image. A training set for this segmentation network may be obtained, which includes images with manually-segmented abnormalities. These may include the same images based on which the training of the classifier of sub-step 202a was conducted, and/or other images, as long as they come with associated manual segmentations, namely—manually-marked borders of each depicted abnormality.

Next in sub-step 202b, the trained segmentation network may be applied to the patient images classified as "abnormal" in sub-step 202a, in order to segment the one or more abnormalities depicted in each of these images.

As an alternative to sub-steps 202a-b, explicit classification of images is not performed, and instead only segmentation of one or more abnormalities is done—with the classification as "abnormal" being only implicit. That is, in sub-step 202c, a segmentation network may be trained based on images that were manually segmented according to the following instructions given to the experts: segment only features which you consider as abnormalities, and refrain from segmenting anything else. This way, the segmentation itself inherently implies that the expert who performed the segmentation deemed the segmented feature to be an abnormality.

Next in sub-step 202c, this trained segmentation network may be applied to an image of a patient, to segment one or more abnormalities depicted in the image, or to segment nothing (or return a null results) if an abnormality is not present. This segmentation may be repeated for multiple images of multiple patients. Images for which the segmentation network has outputted no segmentation are optionally added to the enriched training set, since these images likely require no further analysis to conclude that they are completely devoid of any abnormalities. To better ensure that this is the case, manual review of these images may be conducted, if so desired.

As sub-step 202b or sub-step 202c conclude, there is provided an interim pool 205 of abnormal images of multiple patients, in each of which one or more abnormalities are segmented.

In a step 206, it is determined whether the one or more abnormalities in the images of the interim pool have remained temporally unchanged. This determination may be based on an older medical image 208 of each of the patients.

To this end, each image in the interim pool may have an acquisition date associated with it (such as in metadata embedded inside the image file, or in external metadata otherwise associated with the image file), and a query is made in one or more relevant image collections, to locate an image of the same patient with an earlier acquisition date.

Optionally, the query also defines the image modality and/or the depicted anatomy (e.g., mammography, thoracic CT, lumbar MRI, etc.), to ensure that only relevant images of the patient are returned.

The earlier acquisition date may be defined as a date distant enough to greatly increase the chances that the abnormality(ies) of that patient have been given enough time to evolve. For example, most malignant lesions normally take at least a few weeks, and sometimes at least a few months, to evolve in a manner which is observable in medical imagery. Accordingly, the image date or date range defined in the query may be set to reflect the minimal duration in which it is believed, based on the pertinent medical literature, that a problematic (e.g., malignant) abnormality would have evolved sufficiently for this to be detected. If the abnormality has not evolved in that duration, it is likely not to be problematic (e.g., malignant).

Assume, for example, that the interim pool included a right-side mammogram of Patient X, dated Jan. 1, 2020. The query was defined to locate any image of Patient X which is older than Jul. 1, 2019 (six months earlier), and which is a right-side mammogram. The query returned a right-side mammogram of Patient X from Mar. 4, 2019. In this exemplary scenario, step 206 may include comparing each segmented abnormality in the Jan. 1, 2020 (newer) image with a corresponding area in the Mar. 4, 2019 (older) image. If the older image turns out to include the same feature in the same area—such as having the same size, color, and/or texture—then it is highly likely that the abnormality detected in the newer image is actually an insignificant one, and vice versa.

The definition of the "same feature" and "same area" may include some relaxation of parameters on which the temporal change detection is based, such as size and/or texture, to account for small variations that may result from the acquisition equipment and/or from insignificant biological or anatomical changes. For example, a temporal size increase of up to 30%, and/or a temporal texture change of up to 50%, may be allowed. Each integer value inside these ranges represents a separate embodiment of the invention. Size may be quantified and compared based, for example, on a pixel count. Texture may be quantified and compared based, for example, on any texture descriptor known in the machine vision field, such as Haralick texture features, Local Binary Pattern (LBP) operator, or Gabor filter analysis, to name a few examples, or on simpler image analysis metrics such as histogram analysis or average color analysis of the segmented abnormality(ies) versus the corresponding area. Any other conventional method for quantifying and comparing size and/or texture (with color being a special case of texture) may be used.

The magnitude of allowed size and/or texture changes may be defined as a function of time, such that changes are forgiven if they have evolved slowly, and vice versa. The magnitude of such changes may alternatively or additionally be defined by a user of method 200, based on, for example, known equipment deviations, exposure parameters indicated for each image file, clinical considerations, and/or the like. Based on such considerations, the percent value of allowed changes may even exceed the ranges listed above.

If it is determined, in step 206, that the one or more abnormalities in the pertinent image of the interim pool have not remained temporally unchanged, then this image may be ignored or discarded 210.

If, on the other hand, it is determined that the one or more abnormalities in the pertinent image of the interim pool have remained temporally unchanged, then this image may proceed to a step 212. In step 212, the image is sanitized, to remove the one or more abnormalities depicted in it. This may be performed, for example, using any inpainting technique known in the art, which replaces the pixel contents of the segmented area with other contents that make the image appear natural and complete. Alternatively, the inpainting may simply include replacing all pixels in the segmented area with uniformly-colored pixels. A suitable inpainting technique may be selected by a user of method 200 as desired.

After all the images in the interim pool have been processed by step 206, and the relevant images have been inpainted in step 212, the inpainted images may be used to enrich 214 a new training set, to which they are added with a "normal" label (or any other label denoting the same). Additional images may be added to the new training set from a different source, to serve as examples of one or more additional classes, such an "abnormal" class and/or the like.

The new training set may be aimed, for example, at training 216 a new classifier to detect malignancies, premalignancies, and/or other abnormalities. Such abnormalities may be of a different type, of course, than the ones detected in step 202.

The enrichment of the new training set with the inpainted images may spare the need to conduct tedious searches for images that are originally clean and devoid of abnormalities, or to procure such costly images—which are often in short supply.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of a numerical range should be considered to have specifically disclosed all the possible subranges as well as individual numerical values within that range. For example, description of a range from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising operating at least one hardware processor to:
    automatically detect, using at least one machine learning algorithm, one or more abnormalities depicted in a medical image of a patient;
    automatically determine whether the one or more abnormalities have remained temporally unchanged, based on an older medical image of the patient; and
    upon determining that the one or more abnormalities have remained temporally unchanged:
        automatically inpaint the one or more abnormalities in the medical image, and
        add the inpainted medical image, with a label denoting that the inpainted medical image is normal, to a new training set for a new machine learning classifier.

2. The method of claim 1, wherein the detection of the one or more abnormalities by the at least one machine learning algorithm comprises:
    applying a machine learning classifier to the medical image of a patient, wherein the machine learning classifier is configured to classify medical images as normal or abnormal, and wherein the application of the machine learning classifier to the medical image results in classification of the medical image as abnormal; and
    segmenting the one or more abnormalities in the medical image, using an artificial neural network (ANN) configured for segmentation.

3. The method of claim 2, further comprising:
    prior to applying the machine learning classifier: training the machine learning classifier to detect abnormalities, based on a training set which comprises medical images that are each manually labeled as normal or abnormal; and prior to segmenting the one or more abnormalities: training the ANN to segment abnormalities, based on a training set which comprises medical images in which abnormalities are manually segmented.

4. The method of claim 2, wherein:
the determination of whether the one or more abnormalities have remained temporally unchanged comprises comparing the segmented one or more abnormalities with a corresponding area in the older medical image.

5. The method of claim 1, wherein the detection of the one or more abnormalities by the at least one machine learning algorithm comprises:
segmenting the one or more abnormalities in the medical image, using an artificial neural network (ANN) configured for segmentation of abnormalities.

6. The method of claim 5, further comprising:
prior to segmenting the one or more abnormalities: training the ANN to segment abnormalities, based on a training set which comprises medical images in which abnormalities are manually segmented.

7. The method of claim 5, wherein:
the determination of whether the one or more abnormalities have remained temporally unchanged comprises comparing the segmented one or more abnormalities with a corresponding area in the older medical image.

8. The method of claim 1, wherein:
the determination of whether the one or more abnormalities have remained temporally unchanged is based on detecting at least one of: a size change, a color change, and a texture change.

9. The method of claim 1, wherein:
the at least one machine learning algorithm is configured to detect abnormalities that are selected from the group consisting of: benign lesions, artificial implants, injuries, and interventional tissue modifications.

10. The method of claim 1, further comprising:
repeating the steps of claim 1 for multiple medical images of multiple patients, wherein the inpainted medical images are used to enrich a single new training set;
manually labeling each of the inpainted medical images as normal;
adding, to the single new training set, additional medical images that are labeled as abnormal; and
training a new machine learning classifier based on the single new training set.

11. The method of claim 10, wherein the new machine learning classifier is configured, following its training, to detect abnormalities that are selected from the group consisting of: malignant lesions, and premalignant lesions.

12. A system comprising:
(a) at least one hardware processor; and
(b) a non-transitory computer-readable storage medium having program code embodied therewith, the program code executable by said at least one hardware processor to:
automatically detect, using at least one machine learning algorithm, one or more abnormalities depicted in a medical image of a patient,
automatically determine whether the one or more abnormalities have remained temporally unchanged, based on an older medical image of the patient, and
upon determining that the one or more abnormalities have remained temporally unchanged:
automatically inpaint the one or more abnormalities in the medical image, and
add the inpainted medical image, with a label denoting the inpainted medical image is normal, to a new training set for a new machine learning classifier.

13. The system of claim 12, wherein the detection of the one or more abnormalities by the at least one machine learning algorithm comprises:
applying a machine learning classifier to the medical image of a patient, wherein the machine learning classifier is configured to classify medical images as normal or abnormal, and wherein the application of the machine learning classifier to the medical image results in classification of the medical image as abnormal; and
segmenting the one or more abnormalities in the medical image, using an artificial neural network (ANN) configured for segmentation,
wherein the determination of whether the one or more abnormalities have remained temporally unchanged comprises comparing the segmented one or more abnormalities with a corresponding area in the older medical image.

14. The system of claim 12, wherein the detection of the one or more abnormalities by the at least one machine learning algorithm comprises:
segmenting the one or more abnormalities in the medical image, using an artificial neural network (ANN) configured for segmentation of abnormalities,
wherein the determination of whether the one or more abnormalities have remained temporally unchanged comprises comparing the segmented one or more abnormalities with a corresponding area in the older medical image.

15. The system of claim 12, wherein:
the determination of whether the one or more abnormalities have remained temporally unchanged is based on detecting at least one of: a size change, a color change, and a texture change.

16. The system of claim 12, wherein the program code if further executable by said at least one hardware processor to:
repeat the execution of the program code of claim 12 for multiple medical images of multiple patients, wherein the inpainted medical images are used to enrich a single new training set;
manually label each of the inpainted medical images as normal;
add, to the single new training set, additional medical images that are labeled as abnormal; and
train a new machine learning classifier based on the single new training set.

17. A computer program product comprising a non-transitory computer-readable storage medium having program code embodied therewith, the program code executable by at least one hardware processor to:
automatically detect, using at least one machine learning algorithm, one or more abnormalities depicted in a medical image of a patient,
automatically determine whether the one or more abnormalities have remained temporally unchanged, based on an older medical image of the patient, and
upon determining that the one or more abnormalities have remained temporally unchanged:
automatically inpaint the one or more abnormalities in the medical image, and
add the inpainted medical image, with a label denoting that the inpainted medical image is normal, to a new training set for a new machine learning classifier.

18. The computer program product of claim 17, wherein the detection of the one or more abnormalities by the at least one machine learning algorithm comprises:
  applying a machine learning classifier to the medical image of a patient, wherein the machine learning classifier is configured to classify medical images as normal or abnormal, and wherein the application of the machine learning classifier to the medical image results in classification of the medical image as abnormal; and
  segmenting the one or more abnormalities in the medical image, using an artificial neural network (ANN) configured for segmentation,
  wherein the determination of whether the one or more abnormalities have remained temporally unchanged comprises comparing the segmented one or more abnormalities with a corresponding area in the older medical image.

19. The computer program product of claim 17, wherein the detection of the one or more abnormalities by the at least one machine learning algorithm comprises:
  segmenting the one or more abnormalities in the medical image, using an artificial neural network (ANN) configured for segmentation of abnormalities,
  wherein the determination of whether the one or more abnormalities have remained temporally unchanged comprises comparing the segmented one or more abnormalities with a corresponding area in the older medical image.

20. The computer program product of claim 17, wherein:
  the determination of whether the one or more abnormalities have remained temporally unchanged is based on detecting at least one of: a size change, a color change, and a texture change.

* * * * *